United States Patent [19]

Chauvette

[11] 4,008,228
[45] Feb. 15, 1977

[54] PROCESS FOR PREPARING 3-METHYL-3-CEPHEM ANTIBIOTICS
[75] Inventor: Robert R. Chauvette, Indianapolis, Ind.
[73] Assignee: Eli Lilly and Company, Indianapolis, Ind.
[22] Filed: July 14, 1975
[21] Appl. No.: 595,965

Related U.S. Application Data
[63] Continuation of Ser. No. 205,291, Dec. 6, 1971.
[52] U.S. Cl. .............................. 260/243 C; 424/246
[51] Int. Cl.$^2$ ...................................... C07D 501/02
[58] Field of Search ................................ 260/243 C
[56] References Cited
UNITED STATES PATENTS
3,932,393  1/1976  Chaunette .................. 260/243 C Primary Examiner—Nicholas S. Rizzo
Attorney, Agent, or Firm—William B. Scanlon; Everet F. Smith

[57] ABSTRACT

7-Acylamino-3-methyl-3-cephem-4-carboxylic acids and esters are prepared via the reductive cleavage of a 3-thio substituted 2-cephem-4-carboxylic acid or ester with hydrogen and Raney nickel or zinc in formic acid and DMF to provide reduction product mixtures of the corresponding 7-substituted 3-methyl-2-cephem-4-acid or ester (I) and 3-exomethylenecepham-4-acid or ester (II). Reduction product mixtures are separable via chromatography and individual I and II are isomerized to 3-methyl-3-cephem antibiotics.

6 Claims, No Drawings

PROCESS FOR PREPARING 3-METHYL-3-CEPHEM ANTIBIOTICS

This is a continuation, of application Ser. No. 205,291, filed Dec. 6, 1971.

BACKGROUND OF THE INVENTION

This invention is concerned with the cephalosporin antibiotics. In particular it is concerned with a process for the preparation of deacetoxycephalosporanic acids, 3-methyl-7-acylamino-3-cephem-4-carboxylic acids.

Heretofore the 3-methyl-3-cephem ring system of the deacetoxycephalosporanic acids has been elaborated via a penicillin sulfoxide rearrangement as described by U.S. Pat. No. 3,275,626 and by the acylation of 7-aminodeacetoxycephaloxporanic acid, 7-ADCA.

The prior art is replete with descriptions of 3-thiosubstituted methyl-3-cephem compounds commonly prepared by the nucleophilic displacement reaction of a cephalosporanic acid with a sulfur nucleophile.

For example the compounds described by U.S. Pat. Nos. 3,239,515, 3,239,516, 3,446,803, 3,516,997, 3,243,435, 3,258,461 and 3,261,832 are representative of such 3-thiosubstituted methyl-3-cephem cephalosporins.

It is an object of this invention to provide a process for the preparation of deacetoxycephalosporanic acids. In particular it is an object of this invention to provide a process for the preparation of deacetoxycephalosporanic acids which employs as starting materials the readily available 3-thio substituted methyl-2-cephem compounds of the prior art.

SUMMARY OF THE INVENTION

This invention relates to a novel process for the preparation of 7-acylamino-3-methyl-3-cephem-4-carboxylic acid antibiotics commonly referred to as deacetoxycephalosporanic acids. In particular this invention relates to a process for converting a 7-acylamino-3-acetoxymethyl-2-cepham-4-carboxylic acid to a 7-acylamino-3-methyl-3-cephem-4-carboxylic acid.

According to this invention a 7-amino or 7-acylamino-3-acetoxymethyl-2-cephem-4-carboxylic acid is reacted with a sulfur nucleophile to provide, via nucleophilic displacement of the 3-acetoxy group, a 3-thio-substituted methyl-2-cephem-4-carboxylic acid. The 3-thio-substituted methyl-2-cephem compounds thus obtained undergo reductive cleavage under catalytic hydrogenation conditions and under chemical reduction conditions with zinc in the presence of formic acid and dimethylformamide (DMF) to provide a mixture of cleavage products comprising a 3-methyl-2-cephem product and a 3-exomethylenecepham product. The products thus obtained can be isomerized to 3-methyl-3-cephem compounds, the deacetoxycephalosporanic acids or esters. For example, the 3-methyl-2-cephem compound obtained as the predominant product by catalytic hydrogenation of a 3-thio-substituted methyl-2-cephem compound can be isomerized via the formation of its sulfoxide followed by reduction of the sulfoxide by known procedures. The 3-exomethylenecepham reductive cleavage product can be isomerized to a 3-cephem antibiotic by commingling the reduction product with a tertiary amine such as triethylamine in the presence of an aprotic solvent such as dimethylacetamide according to the method described by copending U.S. application Ser. No. 118,941 filed, Feb. 25, 1971 now U.S. Pat. No. 3,932,393.

The 7-acylamino-3-methyl-3-cephem-4-carboxylic acids provided by the process of this invention are known antibiotic substances of the deacetoxycephalosporanic acid class.

DETAILED DESCRIPTION

According to the process of this invention a deacetoxycephalosporanic acid is prepared from a cephalosporanic acid via isomerization of the cephalosporanic acid to a 2-cephem compound followed by nucleophilic substitution of the 3-acetoxymethyl group with a thio nucleophile. The 3-thio-substituted methyl-2-cephem product is then subjected to the reduction conditions as hereinafter described to provide a 3-methyl-2-cephem reduction product and a 3-exomethylenecepham reduction product. Both products can thereafter be isomerized to the deacetoxycephalosporanic acids by known procedures.

The isomerization of a cephalosporanic acid, a 3-cephem, to a 2-cephem is accomplished by well known procedures, for example, the procedres described by *J. Chem. Soc.* (1966) 1142; *J. Org. Chem.*, 35, 2429 (1970) and *J. Am. Chem. Soc.*, 85, 1896 (1963).

The nucleophilic displacement reaction of the 3-acetoxymethyl-2-cephem isomerization product is carried out according to the procedures by *J. Chem. Soc.* (1965) 5015, and U.S. Pat. Nos. 3,446,803; 3,278,531; 3,261,832; 3,239,516 and 3,243,435.

According to the process of this invention a 3-thio-substituted methyl-2-cephem compound represented by the Formula I.

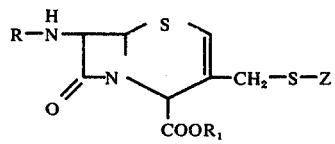

FORMULA I is reduced, either under the conditions of catalytic hydrogenation or under chemical reduction conditions with metallic zinc in the presence of formic acid and dimethylformamide, to provide a compound represented by the formula

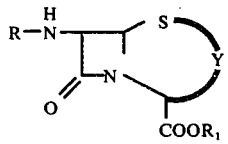

where in the above formulae

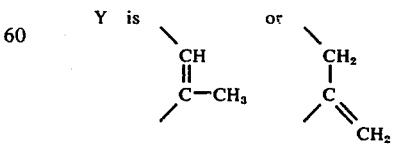

R is hydrogen, $C_1$–$C_8$ alkanoyl, benzoyl, aminoadipoyl, protected aminoadipoyl, or a group represented by the formula

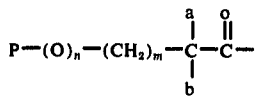

wherein P is α-thienyl, β-thienyl, α-furyl, β-furyl, phenyl or substituted phenyl,
n is 0 or 1
m is 0 or an integer of from 1 to 3,
a is hydrogen or $C_1$–$C_3$ alkyl,
b is hydrogen, $C_1$–$C_3$ alkyl, hydroxy, protected hydroxy, amino or protected amino;
with the limitation that when n is 1, P is phenyl or substituted phenyl and b is hydrogen or $C_1$–$C_3$ alkyl; $R_1$ is hydrogen, a carboxylic acid protecting group, or an alkali metal cation or alkaline earth metal cation; Z is
$C_2$–$C_4$ alkanoyl,
$C_2$–$C_4$ haloalkanoyl,
benzoyl,
substituted benzoyl,
$C_1$–$C_4$ lower alkyl,
$C_1$–$C_{12}$ alkoxythionocarbonyl,
an amidino group of the formula

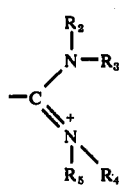

wherein $R_2$, $R_3$, $R_4$ and $R_5$ are the same or different and represent hydrogen, $C_1$–$C_6$ alkyl, phenyl, aralkyl, substituted phenyl or substituted aralkyl, a thiocarbamoyl group of the formula

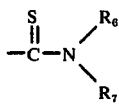

wherein $R_6$ and $R_7$ when taken separately are the same or different and are hydrogen, $C_1$–$C_6$ alkyl, or phenyl and $R_6$ and $R_7$ when taken together form a 4 or 5 membered alkylene, azaalkylene, oxalkylene or thioalkylene bridge, a monocyclic heteroaryl group, or a sulfo group represented by the formula

—$SO_3^-$ $M^+$ wherein $M^+$ is an alkali metal cation or alkaline earth metal cation; and when Z is amidino or substituted amidino, $R_1$ is hydrogen and Z is —$SO_3^-$ $M^+$, $R_1$ is $M^+$.

As used herein the term "$C_1$–$C_8$ alkanoyl," refers to formyl, acetyl, propionyl, butyryl, pivaloyl, hexanoyl, heptanoyl and like groups represented by the formula

where R is hydrogen or a straight or branched chained alkyl group having from 1 to 7 carbon atoms. The term "protected aminoadipoyl" means the α-aminoadipoyl group where the α-amino group is substituted by a commonly employed amino protecting group as for example, t-butyloxycarbonyl, t-amyloxycarbonyl, benzyloxycarbonyl, adamantyloxycarbonyl, trichloroethoxycarbonyl, chloroacetyl, dichloroacetyl, phthaloyl, propionyl, the enamine formed with pentane-1,3-dione, and like amino protecting groups.

Representative of the 7-acylamino group R, when R is

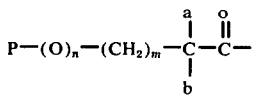

are phenylacetyl, phenoxyacetyl, α-thienylacetyl, β-thienylacetyl, α-furylacetyl, β-furylacetyl, 4-methylphenylacetyl, 4-chlorophenylacetyl, 4-methylphenylacetyl, 4-chlorophenylacetyl, 4-methoxyphenylacetyl, 4-methoxy-3-ethoxyphnmylacetyl, phenylglycyl, β-phenylpropionyl, α-methylphenylacetyl, α,α-dimethylphenylacetyl, α-hydroxyphenylacetyl, α-n-propylphenylacetyl, 3-hydroxyphenylacetyl, 4-hydroxyphenylacetyl, 3-hydroxyphenylglycyl, 4-hydroxyphenylglycyl, 4-t-butylphenoxyacetyl, 3-phenoxypropionyl, 4-chlorophenoxyacetyl, 3-bromophenoxyacetyl, α-aminothienylacetyl, 4-hydroxyphenylglycyl, 3-hydroxyphenylglycyl, and like 7-acylamino groups.

The term, "protected hydroxy," refers to the hydroxyl group protected by such groups as formyl, trichloroacetyl, t-butyl, benzyl, benzhydryl and like hydroxy protecting groups.

"Substituted phenyl", as indicated previously refers to halophenyl, phenyl substituted by $C_1$–$C_4$ lower alkyl, $C_1$–$C_4$ lower alkoxy and hydroxy. The term, $C_1$–$C_4$ lower allkyl, refers to methyl, ethyl, n-propyl, isopropyl, n-butyl, sec-butyl, isobutyl and t-butyl. $C_1$–$C_4$ lower alkoxy, means methoxy, ethoxy, n-propoxy, isopropoxy, n-butoxy, iso-butoxy, sec-butoxy and t-butoxy groups.

With reference to $R_1$ in the above formulae, the term, a carboxylic acid protecting group refers to the commonly used carboxylic acid protecting ester forming groups such as $C_1$–$C_4$ alkyl, benzyl, benzhydryl, p-nitrobenzyl, 3,5-dimethoxybenzyl, 2,2,2-trichloroethyl and like ester forming moieties. When $R_1$ is an alkali or alkaline earth metal cation; such cations as the lithium, sodium, potassium and calcium cations are representative of $R_1$.

With reference to the 3-substituent, —$CH_2$—S—Z, in the above Formula I; when Z is $C_2$–$C_4$ alkanoyl, Z represents acetyl, propionyl, butyryl and like radicals. When Z is $C_2$–$C_4$ haloalkanoyl, Z represents for example, chloracetyl, trichloroacetyl, β-chloropropionyl, α-chlorobutyryl and the like.

The term substituted benzoyl within the definition of Z refers to benzoyl substituted by halogen, $C_1$–$C_4$ lower alkyl, $C_1$–$C_4$ lower alkoxy or hydroxy. The term $C_1$–$C_{12}$ alkoxythionocarbonyl refers to such groups as methoxythionocarbonyl, ethoxythionocarbonyl, n-propoxythionocarbonyl, t-butoxythionocarbonyl, n-amyloxythionocarbonyl, n-octyloxythionocarbonyl, n-decyloxythionocarbonyl, n-dodecyloxythionocarbonyl, n-hexyloxythionocarbonyl, and like groups.

When Z represents an amidino group, the isothiouronium salts or substituted isothiouronium salts represented thereby are prepared by the reaction of thiourea or a substituted thiourea with the desired 7-acylamino-3-acetoxymethyl-2-cephem-4-carboxylic acid wherein $R_1$ is hydrogen according to the method described by U.S. Pat. No. 3,278,531 and as illustrated by the following equation

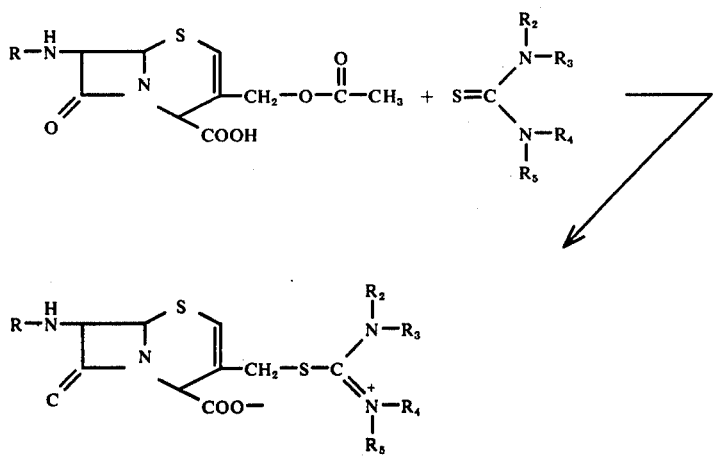

Illustrative of the thiourea compounds which can be employed in the above described reaction are thiourea, N,N'-diphenylthiourea, tetramethylthiourea, n-butylthiourea, N,N'-diethylthiourea, N,N'-di-n-hexylthiourea, N,N'-dibenzylthiourea, N-(2-phenylethyl)thiourea, N-methyl-N'-n-butylthiourea and phenylthiourea.

When Z in Formula I is a thiocarbamoyl group and $R_6$ and $R_7$ are taken separately then such groups as N-methylthiocarbamoyl, N,N-dimethylthiocarbmoyl, N,N-di-n-butylthiocarbamoyl, N-isopropylthiocarbamoyl, N,N-di-n-hexylthiocarbamoyl, thiocarbamoyl, N,N-diphenylthiocarbamoyl, N-phenyl-N-methylthiocarbamoyl, N-phenyl-N-ethylthiocarbamoyl, N,N-diethylthiocarbamoyl, N-amyl-N-methylthiocarbamoyl, N-phenyl-N-n-butylthiocarbamoyl, and N-propylthiocarbamoyl are representative. When $R_6$ and $R_7$ are taken together then Z represents such groups as pyrrolidinothiocarbonyl, piperidinothiocarbonyl, morpholinothiocarbonyl, thiomorpholinothiocarbonyl and piperazinothiocarbonyl.

The term, "monocyclic heteroaryl group", as used herein refers to the 5 and 6 membered heterocyclic ring moieties such as 2-, or 3-pyridyl, 2-pyrimidyl, 2-imidazolyl, 2-thiazolyl, 2-tetrazolyl, 1-methyl-2-tetrazolyl, 1,3,4-thiadiazolyl, 5-methyl-1,3,4-thiadiazolyl, and like heterocyclic rings.

In the foregoing definitions, hydroxy, amino and carboxy protecting groups, even though exemplified in a limited manner, are not exhaustively defined. Such protecting groups are well known in the art and the use of other groups, not specifically listed, will be recognized as suitable in the present process. The function of such groups is to protect the reactive funtional groups during the process and then be easily removed without disrupting the remainder of the molecule.

When Y in the foregoing formula is

the 7-acylamino-3-methyl-2-cephem-4-carboxylic acids and esters thereof can be represented by the following Formula II ![Formula II]

Likewise when Y is

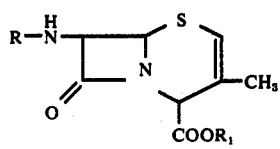

the 7-acylamino-3-methylenecepham-4-carboxylic acids and esters can be represented by the Formula III ![Formula III]

Illustrative of the compounds represented by Formula I are the following.

7-(2-Phenylacetamido)-3-methylthiomethyl-2-cepham-4-carboxylic acid, 7-(2-Phenoxyacetamido)-3-amidinothiomethyl-2-cephem-4-carboxylic acid inner salt, 7-[2-(2-Thienyl)acetamido]-3-ethoxythionocarbonylthiomethyl-2-cephem-4-carboxylic acid, 7-(2-hydroxy-2-phenylacetamido)-3-acetylthiomethyl-2-cepham-4-carboxylic acid 7-(5-amino-5-carboxyvaleramido)-3-benzoylthiomethyl-2-cepham-4-carboxylic acid, 7-(5-tert-butyloxycarbamido-5-carboxyvaleramido)-3-amidinothiomethyl-2-cepham-4-carboxylic acid, inner salt, 7-(2-amino-2-phenylacetamido)-3-n-propoxythioncarbonylthiomethyl-2-cephem-4-carboxylic acid, 7-[2-(3-thienyl)acetamido]-3-chloroacetylthiomethyl-2-cephem-4-carboxylic acid, 7-acetamido-3-(4-methylbenzoylthiomethyl)-2-cephem-4-carboxylic acid, 7-(2-amino-2-phenylacetamido)-3-N,N-dimethylthiocarbamoylthiomethyl-2-cephem-4-carboxylic acid, 7-[2-(2-furyl)acetamido]-3-amidinothiomethyl-2-cephem-4-carboxylic acid, inner salt 7-(α-phenoxypropionamido)-3-morpholinothionocarbonylthiomethyl-2-cephem-4-carboxylic acid, 7-butyramido-3-sulfothiomethyl-2-cephem-4-carboxylic acid disodium salt, tert-butyl 7-[2-amino-2-(3-hydroxyphenyl)acetamido]-3-benzoylthiomethyl-2-cephem-4-carboxylate.

7-amino-3-ethylthiomethyl-2-cephem-4-carboxylic acid, 7-n-caprylamido-3-piperidinothionocarbonylthiomethyl-2-cephem-4-carboxylic acid, 7-(α-phenylbutyramido)-3-isopropoxythionocarbonylthiomethyl-2-cephem-4-carboxylic acid, 7-acetamido-3-[(2-pyridyl)thiomethyl]-2-cephem-4-carboxylic acid, 2,2,2-trichloroethyl 7-(2-phenoxyacetamido)-3-benzoylthiomethyl-2-cephem-4-carboxylate, 7-isovaleramido-3-[(2-pyrimidyl)thiomethyl]-2-cephem-4-carboxylic acid, 7-(2-tert-butyloxycarbamido-2-phenylacetamido)-3-amidinothiomethyl-2-cephem-4-carboxylic acid, inner salt, 7-propionamido-3-phenylamidinothiomethyl-2-cephem-4-carboxylic acid inner salt, 7-amino-3-amyloxythionocarbonylthiomethyl-2-cephem-4-carboxylic acid, 7-(2-tert-butyloxycarbamido-2-phenylacetamido)-3-n-propoxythiono-carbonyl-2-cephem-4-carboxylic acid, 7-(2-acetamido-2-phenylacetamido)-3-N,N-dimethylthiocarbamoylthiomethyl-2-cephem-4-carboxylic acid, benzyl 7-amino-3-ethylthiomethyl-2-cephem-4-carboxylate, 2,2,2-trichloroethyl 7-amino-3-ethoxythionocarbonylthiomethyl-2-cephem-4-carboxylate, 7-amino3-ethoxythionocarbionylthiomethyl-2-cephem-4-carboxylic acid, The 3-thio-substituted methyl-2-cephem compounds of the Formula I, the starting materials for the process of the present invention, are prepared according to known reactions. The compounds of the Formula I are prepared by first isomerizing a cephalosporanic acid to a 3-acetoxymethyl-2-cephem compound and thereafter reacting the 2-cephem compound via a nucleophilic displacement reaction with a sulfur nucleophile to obtain a compound of the Formula I. The methods and procedures for the isomerization reaction and the nucleophilic displacement reaction are described by Webber, et al. *J. Am. Chem. Soc.*, 91, 5674 (1969); Murphy and Koehler, *J. Org. Chem.* 35, 2429 (1970); Cocker, et al. *J. Chem. Soc.* (1965) 5015 and Cocker, et al. *J. Chem. Soc.* (1966) 1142.

A 3-thio-substited methyl-2-cephem compound represented by the Formula I is reduced under catalytic hydrogenation conditions according to the present process in the following manner. The compound is dissolved in an inert solvent and hydrogenated in the presence of a hydrogenation catalyst in an atmosphere of hydrogen gas maintaned at a pressure between about atmospheric pressure and 250 lbs. per square inch. The reaction can be carried out conveniently at or about 25° C.; however, the reduction occurs at a more desirable rate at a temperatue of from about 30° C. to about 55° C. Solvents which can be employed in the present process are any commonly used hydrogenation solvents which are unreactive with the starting materials and products and preferably those which are not themselves reduced under the conditions of the hydrogenation. Such solvents include water, tetrhydrofuran, dioxane, the alcoholic solvents, such as methanol, ethanol, and the like, the esters, such as ethyl acetate, methyl propionate, methyl butyrate, isoamyl acetate, amyl acetate, and like esters, alcohols and ethers. The particular solvent employed depends to a certain extent upon the form of the starting material used. For example, when in Formula I $R_1$ is an alkali or alkaline earth metal cation, the salt represented thereby is conveniently dissolved in water. Mixtures of solvents can likewise be employed in the present process; for example, aqueous alcohol, such as 50 percent aqueous ethanol can be employed to advantage.

Raney nickel is the preferred hydrogenation catalyst of the present process. Although other forms of nickel catalysts, such as nickel on kieselguhr, can be employed, Raney nickel affords superior yields and the reduction requires less time. Other catalysts, such as Raney cobalt and palladium on carbon can also be employed to prepare compounds of the Formulae II and III.

As previously mentioned, the hydrogenation is carried out under a hydrogen pressure between about 15 and 250 lbs. per square inch. Although the reduction will occur at higher pressures, such higher pressures are not required. The catalytic hydrogenation can be carried out in standard hydrogenation equipment, for example, in a Parr low pressure hydrogenation apparatus. Alternatively, the catalytic hydrogenation can be carried out in an open vessel, in which case hydrogen gas is allowed to pass through a solution of the compound of the Formula I containing in suspension the hydrogenation catalyst.

In a further aspect of the reduction process of this invention, a compound of the Formula I is chemically reduced to provide compounds of the Formulae II and III. The chemical reduction conditions of the present process are as follows. The 3-thio-substituted methyl-2-cephem compound of the Formula I is dissolved in a suitable solvent and finely divided zinc dust is added to the solution. Dimethylformamide is then added to the solution, followed by formic acid. The reduction mixture is then stirred at a temperature between about 0° and about 60° C. for between about 6 hours and 18 hours. Solvents which can be employed in the chemical reduction include water, tetrahydrofuran, dioxane, and other ethers, for example, the dimethylether of ethyleneglycol. Water and ether solvent mixtures can also be employed. In general any solvent in which the starting material is at least partially soluble at the reduction temperature, and which is unreactive with the reduction mixture constituents can be employed. The foregoing solvents are exemplary of the solvents which can be employed.

Generally, zinc dust is employed in excess, and preferably between about 1.5 and 3 grams of zinc dust per gram of compound is desirably employed. Higher amounts of zinc dust can be employed but are usually unnecessary. Although lesser amounts of zinc dust result in longer reduction time and, in certain instances, in lower yields of reduction products, the reduction products can nevertheless be obtained with such lesser amounts.

The amount of formic acid used is not critical provided a sufficient quantity is added to react with the zinc and provide the desired reduction medium.

The chemical reduction of a compound of the Formula I is carried out in the presence of dimethylformamide. The amount of dimethylformamide (DMF) is not critical provided that it is employed in an amount at least equivalent to about 10 percent by weight of the amount of zinc dust employed. However, it is preferable and more convenient to employ larger amounts of DMF and generally about equal volumes of DMF and formic acid are suitable.

In a preferred embodiment of this invention, to a solution of 3-ethoxythionocarbonylthiomethyl-7-[2-(2-thienyl)acetamido]-2-cephem-4-carboxylic acid sodium salt in a solvent mixture of tetrahydrofuran and water was added triethylamine by dropwise addition until the pH was adjusted to pH 8.8. Raney nickel was added to the solution and the mixture was hydrogenated under 45 lbs. psi. of hydrogen pressure on a Parr low pressure hydrogenation apparatus. The reduction was conducted at room temperature for a period of about 18 hours. The catalyst was filtered and washed on a filter with tetrahydrofuran. The filtrate and wash were combined and added to a mixture of 5 percent hydrochloric acid and ethyl acetate. The organic layer was separated and was washed with water before drying. The dried organic layer was evaporated to dryness in vacuo to yield a crystalline residue containing predominantly, 7-[2-(2-thienyl)acetamido]-2-cephem-3-methyl-4-carboxylic acid.

In a further embodiment of the present process, 3-amidinothiomethyl-7-[2-(2-thienyl)acetamido]-2-cephem-4-carboxylic acid inner salt was dissolved in a solvent mixture of tetrahydrofuran, formic acid, dimethylformamide and water. To this solution was added zinc dust, and the mixture was stirred overnight at room temperature. Following work up in a conventional manner, there was recovered a crystalline mixture comprising approximately a 3 to 2 mixture by weight of the corresponding 3-methyl-2-cephem compound and the 3-exomethylenecepham compound as represented by the Formulae II and III respectively where R is 2-(2-thienyl)acetamido and $R_1$ is hydrogen.

When the reduction process of this invention is carried out with zinc in the presence of formic acid and dimethylformamide the reduction product, a 3-methyl-2-cephem compound is produced along with a 3-exomethylenecepham compound. The predominant reduction product obtained is more often the 3-methyl-2-cephem compound. The reduction product mixture comprising the two previously mentioned isomers is usually obtained as a crystalline mixture. The individual reduction products can be separated and each purified by fractional recrystallization or by chromatography of the reduction product mixture over silica.

The 3-exomethylenecepham reduction product can be isomerized to a deacetoxycephalosporanic acid according to the procedure described by copending application Ser. No. 118,941, filed Feb. 25, 1971. According to this method, a 3-exomethylenecepham reduction product is dissolved or suspended in a highly polar aprotic solvent, preferably dimethylacetamide, containing a tertiary amine having a pK'a value of at least pK'a 9.5, preferably triethylamine, and the isomerization mixture allowed to stir for about 18 hours. The mixture is then poured into water and a water immiscible organic solvent such as ethyl acetate is then added to the aqueous mixture. The mixture is then acidified to about ph2 and the ethyl acetate layer containing the isomerization product is separated and dried. Evaporation of the extract provides the isomerization product, a 3-methylcephem compound.

When in the formula I, Z is a sulfo group, chemical reduction in the presence of zinc, formic acid and dimethylformamide fails to provide any substantial amount of 3-methyl-2-cephem reduction product. However, when reduction is carried out with Raney nickel and hydrogen, the 3-sulfo derivative provides substantial yields of the 3-methyl-2-cephem reduction product. Apparently, in the instance where zinc, formic acid and dimethylformamide is the reduction procedure, the acidity of the reduction mixture results in untoward side products thereby preventing reduction to occur in the normal course.

Reduction of a compound of the Formula I with Raney nickel and hydrogen in most instances affords as the predominant product a 3-methyl-2-cephem reduction product.

The 3-methyl-2-cephem reduction products of this invention have characteristic nuclear magnetic resonance spectra.

The 3-methyl-2-cephem compounds provided by this invention can be converted to deacetoxycephalosporanic acids (3-methyl-3-cephem compounds) according to methods well known to those skilled in the art. Accordingly, the 3-methyl-2-cephem compound is oxidized by the reaction with an organic peracid, preferably m-chloroperbenzoic acid, to provide the corresponding sulfoxide. As is known and described in the literature, the formation of the cephalosporin sulfoxide is accompanied by isomerizaton of the double bond from the $\Delta^2$- to the $\Delta^3$- position. The 3-methyl-3-cephem sulfoxide obtained thereby is then reduced according to the methods and procedures described by copending U.S. application Ser. No. 764,925, filed Oct. 3, 1968 now U.S. Pat. No. 3,641,014. The 3-methyl-3-cephem reduction products, deacetoxycephalosporanic acids, are well known antibiotics useful for inhibiting the growth of microorganisms pathogenic to both animal and plant life. For example, when in the Formula I, R is the 2-amino-2-phenylacetyl group, the reduction method provided by this invention affords the known and useful antibiotic cephalexin.

The following general reaction scheme illustrates the process and procedures employed in this invention and illustrates further the usefulness of the process provided herein for converting a cephalosporanic acid into a deacetoxycephalosporanic acid via the intermediates and processes described.

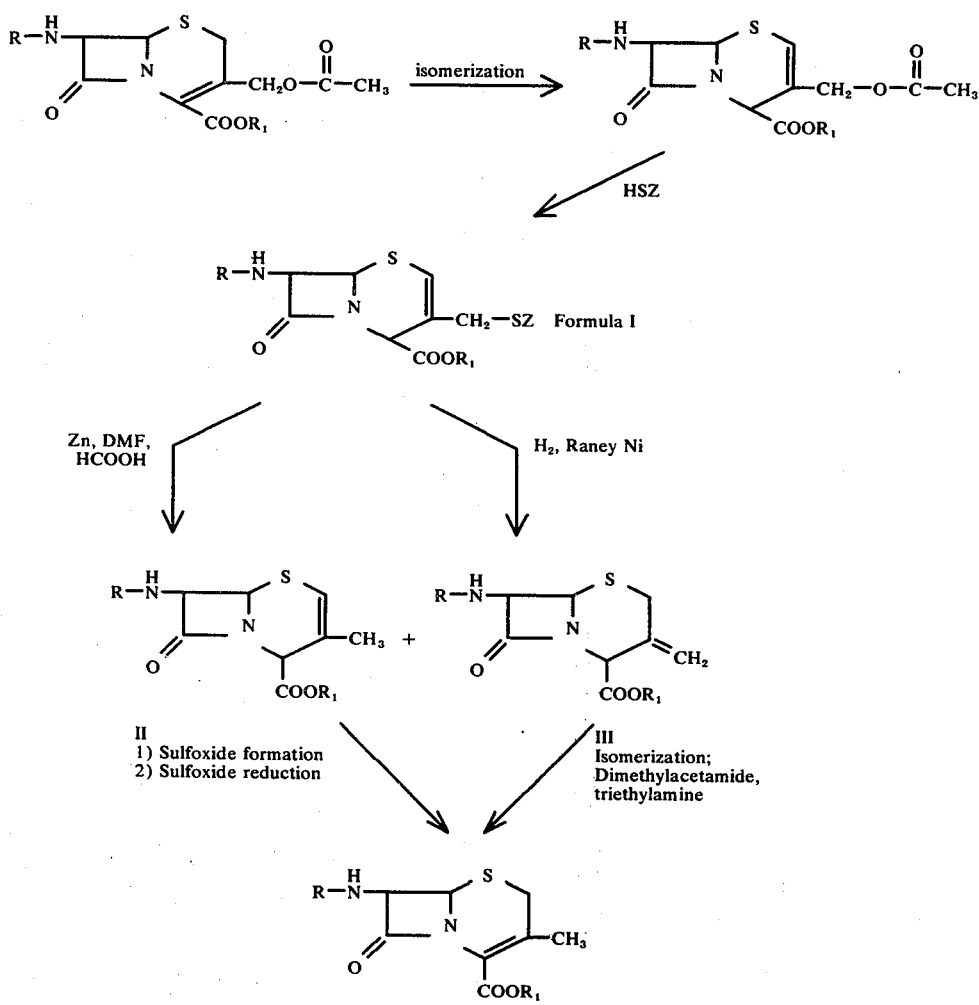

Illustrative of the 3-methyl-2-cephem-4-carboxylic acids and esters which are provided by this invention are the following:

7-(2-phenylacetamido)-3-methyl-2-cephem-4-carboxylic acid,
7-(2-phenoxyacetamido)-3-methyl-2-cephem-4-carboxylic acid,
benzyl 7-(2-phenoxyacetamido)-3-methyl-2-cephem-4-carboxylate,
2,2,2-trichloroethyl 7-[2-(2-thienyl)acetamido]-3-methyl-2-cephem-4-carboxylate,
7-acetamido-3-methyl-2-cephem-4-carboxylic acid,
7-amino-3-methyl-2-cephem-4-carboxylic acid,
benzyl 7-amino-3-methyl-2-cephem-4-carboxylate,
7-(5-amino-5-carboxyvaleramido)-3-methyl-2-cephem-4-carboxylic acid,
7-(2-amino-2-phenylacetamido)-3-methyl-2-cephem-4-carboxylic acid,
7-(2-hydroxy-2-phenylacetamido)-3-methyl-2-cephem-4-carboxylic acid,
7-(2-propionamido-2-carboxyvaleramido)-3-methyl-2-cephem-4-carboxylic acid,
7-(2-acetamido-2-carboxyvaleramido)-3-methyl-2-cephem-carboxylic acid,
benzhydryl 7-(2-phenylacetamido)-3-methyl-2-cephem-4-carboxylate and 7-propionamido-3-methyl-2-cephem-4-carboxylic acid. Illustrative of the 3-exomethylenecepham-4-carboxylic acids and esters represented by the Formula III and provided by the present process are the following:

7-amino-3-methylenecepham-4-carboxylic acid,
7-(2-phenoxyacetamido)-3-methylenecepham-4-carboxylic acid,
7-[2-(2-thienyl)acetamido]-3-methylenecepham-4-carboxylic acid,
7-(5-amino-5-carboxyvaleramido)-3-methylenecepham-4-carboxylic acid,
7-(2-phenylacetamido-3-methylenecepham-4-carboxylic acid,
2,2,2-trichloroethyl 7-(2-phenoxyacetamido)-3-methylenecepham-4-carboxylate,
7-(2-hydroxy-2-phenylacetamido)-3-methylenecepham -4-carboxylic acid,
7-(2-amino-2-phenylacetamido)-3-methylenecepham-4-carboxylic acid,
benzyl 7-(2-phenoxyacetamido)-3-methylenecepham-4-carboxylate,
methyl 7-[2-(2-thienyl)acetamido]-3-methylenecepham-4-carboxylate,
7-acetamido-3-methylenecepham-4-carboxylic acid,
7-n-butryamido-3-methylenecepham-4carboxylic acid,
2,2,2-trichloroethyl 7-amino-3-methylenecepham-4-carboxylate, The following examples more fully illustrate the process and procedures of this invention.

EXAMPLE 1

To a solution of 2.2 g. (29 mmoles) of thiourea in 40 ml. of water was added 7.9 g. (19 mmoles) of 7-[2-(2-thienyl)acetamido]-2-cephem-3-acetoxymethyl-4-carboxylic acid sodium salt. The pH of the solution was adjusted to pH 7 by the addition of 1N sodium hydroxide. The solution was then heated in a water bath for 18 hours at a temperature of 60° C. The mixture was cooled to about room temperature and the precipitate which had formed was filtered and was washed on the filter with water. The precipitate was vacuum dried to yield 3.2 g. of 3-amidinothiomethyl-7-[2-(2-thienyl)acetamido]-2-cephem-4-carboxylic acid, inner salt. Elemental analysis calculated for $C_{15}H_{16}N_4O_4S_3$;
 Theory: C, 43.68; H, 3.91; N, 13.59;
 Found: C, 43.48; H, 3.94; N, 13.32.

The above product gave the following nuclear magnetic resonance spectra in D.M.S.O. $d_6$. The following are the tau values observed in the spectrum.

6.22 (s, 2H, side-chain methylene); 5.82 (m, 2H, $C_3$ methylene), 5.38 (s, 1H, $C_4H$), 4.8–4.6 (m,2H, $C_6$ and $C_7$-H); 3.50 (s, 1H, $C_2$-H); 3.09–2.59 (m,3H, aromatic hydrogen) and 1.7 (d, 1H, amide hydrogen).

EXAMPLE 2

To a solution of 950 mg. (2.4 mmoles) of 3-amidinothiomethyl 7-[2-(2-thienyl)acetamido]-2-cephem-4-carboxylic acid, inner salt, in 25 ml. of tetrahydrofuran and 25 ml. of water was added 5 g. of Raney nickel. The solution was hydrogenated in a Paar low pressure hydrogenation apparatus at a hydrogen pressure of 45 psi. at room temperature for about 12 hours. The catalyst was filtered and washed on the filter with tetrahydrofuran. The filtrate and wash solvent were combined and added to a mixture of 5 percent hydrochloric acid and ethyl acetate. The organic layer was separated and was washed with water before drying over magnesium sulfate. The dried layer was evaporated to dryness in vacuum to yield a crystalline residue. The reduction product was shown by thin layer chromatography and nuclear magnetic resonance spectrum to be 7-[2-(thienyl)acetamido]-2-cephem-3-methyl-4-carboxylic acid.

EXAMPLE 3

To a solution of 500 mg. of 7[2-(2-thienyl)acetamido]-3-ethoxythionocarbonylthiomethyl-2-cephem-4-carboxylic acid sodium salt in 25 ml. of tetrahydrofuran and 25 ml. of water was added triethylamine until the pH of the solution was pH 8.8. Five grams of Raney nickel catalyst were added to the solution and the mixture was hydrogenated on a Parr low pressure hydrogenation apparatus for 15 hours under an initial hydrogen pressure of 45 psi. The catalyst was filtered and washed with tetrahydrofuran. The filtrate and wash were combined and added to a mixture of 5% hydrochloric acid and ethyl acetate. The organic layer was separated, washed with water and was dried. The dried ethyl acetate solution was evaporated to dryness in vacuo to yield 7-[2-(2-thienyl)acetamido]-3-methyl-2-cephem-4-carboxylic acid.

EXAMPLE 4

According to the reduction method described by the preceding example, benzyl 3-benzoylthiomethyl-7-[2-(2-thienyl)acetamido]-2-cephem-4-carboxylate was reduced to yield the crystalline reduction product, benzyl 7-[2'-(2-thienyl)acetamido]-3-methyl-2-cephem-4-carboxylate.

EXAMPLE 5

In a solvent mixture of 55 ml. of tetrahydrofuran, 15 ml. of water, 15 ml. of formic acid and 15 ml. of DMF was dissolved 1 g. of 3-amidinothiomethyl-7-[2-(2-thienyl)acetamido]-2-cephem-4-carboxylic acid, inner salt. To the above solution was added 1.4 g. of zinc dust, and the reaction was stirred overnight at room temperature. The reaction mixture was filtered to remove insolubles and the filtrate was concentrated in vacuo. The residue was diluted with water and extracted with ethyl acetate. The ethyl acetate extract was washed with 5 percent hydrochloric acid followed by water and was then dried. The dried extract was evaporated to dryness to yield the reduction product mixture as an amorphous residue. The residue was crystallized from ethyl acetate to yield a crystalline mixture comprising 70 percent of 7-[2-(2-thienyl)acetamido]-3-methyl-2-cephem-4-carboxylic acid and 30 percent of 3-methylene-7-[2-(2-thienyl)acetamido]cepham-4-carboxylic acid as shown by the thin layer chromatogram and the nuclear magnetic resonance spectrum of the crystalline reduction product mixture.

EXAMPLE 6

To a solution of 500 mg. of benzyl 7-[2-(2-thienyl)acetamido]-3-benzoylthiomethyl-2-cephem-4-carboxylate in a mixture of 15 ml. of tetrahydrofuran, 15 ml. of dimethylformamide, 15 ml. of formic acid (90%) and 15 ml. of water was added 700 mg. of zinc dust. The reaction mixture was stirred at room temperature for 18 hours. The reaction mixture was worked up and the reduction products isolated according to the procedures described by Example 5, to yield a crystalline reduction product mixture comprising a 30 to 70% ratio by weight of benzyl 7-[2-(2-thienyl)acetamido]-3-methyl-2-cephem-4-carboxylate and benzyl 7-[2-(2-thienyl)acetamido]-3-methylenecepham-4carboxylate as demonstrated by the NMR spectrum of the crystalline mixture.

I claim:
1. The method for preparing a compound of the formula

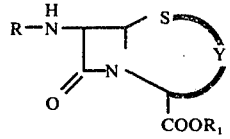

which comprises reducing in an inert solvent a 3-thiosubstituted methyl 2-cephem compound of the formula

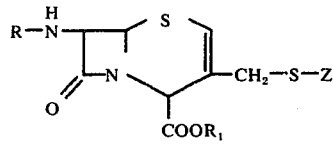

with a reducing agent selected from the group consisting of a) hydrogen in the presence of a nickel, cobalt, or palladium hydrogenation catalyst and b) metallic zinc in the presence of formic acid and dimethylformamide, where in the above formulae Y is or

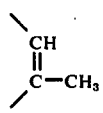   or   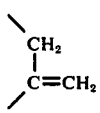

R is hydrogen, $C_1$–$C_8$ alkanoyl, benzoyl, aminoadipoyl, or a group of the formula

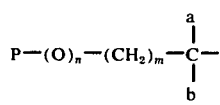

wherein P is α-thienyl, β-thienyl, α-furyl, β-furyl, phenyl, or substituted phenyl substituted by halogen, $C_1$–$C_4$ alkyl, $C_1$–$C_4$ alkoxy or hydroxy,
$n$ is 0 or 1,
$m$ is 0 or an integer of from 1 to 3
$a$ is hydrogen or $C_1$–$C_3$ alkyl,
$b$ is hydrogen, $C_1$–$C_3$ alkyl, hydroxy, or amino; with the limitation that when $n$ is 1, P is phenyl of substituted phenyl and $b$ is hydrogen or $C_1$–$C_3$ alkyl;
$R_1$ is hydrogen, benzyl, benzhydryl, p-nitrobenzyl, 3,5-dimethoxybenzyl or trichloroethyl, or an alkali metal or alkaline earth metal cation;
Z is $C_2$–$C_4$ alkanoyl, $C_2$–$C_4$ haloalkanoyl, benzoyl, substituted benzoyl substituted by halogen, $C_1$–$C_4$ alkyl, $C_1$–$C_4$ alkoxy or hydroxy, $C_1$–$C_4$ lower alkyl, $C_1$–$C_{12}$ alkoxythionocarbonyl, an amidino group of the formula

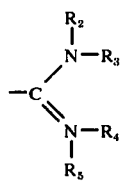

wherein $R_2$, $R_3$, $R_4$ and $R_5$ are the same or different and represent hydrogen, $C_1$–$C_6$ alkyl, phenyl, benzyl, or phenylethyl,
a thiocarbamoyl group of the formula

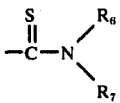

wherein $R_6$ and $R_7$ when taken separately are the same or different and are hydrogen $C_1$–$C_6$ alkyl or phenyl, and when taken together are pyrrolidino, piperidino, morpholino, thiomorpholino or piperazino;
a monocyclic heteroaryl group selected from the group consisting of 2-pyridyl, 3-pyridyl, 2-pyrimidyl, 2-imidazolyl, 2-thiazolyl, 2-tetrazolyl, 1-methyl-2-tetrazolyl, 1,3,4-thiadiazolyl and 5-methyl-1,3,4-thiadiazolyl;
or a sulfo group of the formula

wherein $M^+$ is an alkali metal or alkaline earth metal cation;
and when Z is said amidino group, $R_1$ is hydrogen, and when Z is —$SO_3^-M^+$, $R_1$ is $M^+$.

2. The method of claim 1 wherein the hydrogenation catalyst is Raney nickel.

3. The method of claim 1 wherein the 3-thio-substituted methyl 2-cephem compound is 7-amino-3-ethoxythionocarbonylthiomethyl-2-cephem-4-carboxylic acid.

4. The method of claim 1 wherein the 3-thio-substituted methyl-2-cephem compound is 7-[2-(2-thienyl)acetamido]-3-ethoxythionocarbonylthiomethyl-2-cephem-4-carboxylic acid.

5. The method of claim 1 wherein the 3-thiosubstituted methyl-2-cephem compound is 7-[2-(2-thienyl)acetamido]-3-benzoylthiomethyl-2-cephem-4-carboxylic acid.

6. The method of claim 1 wherein the 3-thiosubstituted methyl-2-cephem compound is 7-[2-(2-thienyl)acetamido]-3-amidinothiomethyl-2-cephem-4-carboxylic acid inner salt.

* * * * *